US007518103B2

(12) United States Patent
Amirav (10) Patent No.: US 7,518,103 B2
(45) Date of Patent: Apr. 14, 2009

(54) PULSED FLOW MODULATION GAS CHROMATOGRAPHY MASS SPECTROMETRY WITH SUPERSONIC MOLECULAR BEAMS METHOD AND APPARATUS

(76) Inventor: Aviv Amirav, 5 Ha Yaar Alley, Hod HaSharon 45269 (IL)

( * ) Notice: Subject to any disclaimer, the term of this patent is extended or adjusted under 35 U.S.C. 154(b) by 184 days.

(21) Appl. No.: 11/758,061

(22) Filed: Jun. 5, 2007

(65) Prior Publication Data
US 2008/0302959 A1 Dec. 11, 2008

(30) Foreign Application Priority Data
Jul. 6, 2006 (IL) .................................... 176724

(51) Int. Cl.
*B01D 59/44* (2006.01)
(52) U.S. Cl. .................. 250/281; 250/282; 250/288; 436/181; 436/173
(58) Field of Classification Search .................. None
See application file for complete search history.

(56) References Cited

U.S. PATENT DOCUMENTS

| | | | | |
|---|---|---|---|---|
| 4,863,491 | A * | 9/1989 | Brandt et al. | 95/29 |
| 5,055,677 | A * | 10/1991 | Amirav et al. | 250/282 |
| 5,223,131 | A * | 6/1993 | Apffel et al. | 210/198.2 |
| 5,686,656 | A * | 11/1997 | Amirav et al. | 73/23.41 |
| 5,742,050 | A * | 4/1998 | Amirav et al. | 250/288 |
| 6,838,288 | B2 * | 1/2005 | Beens | 436/161 |
| 7,091,044 | B2 * | 8/2006 | Cai et al. | 436/161 |
| 7,247,495 | B2 * | 7/2007 | Amirav | 436/173 |
| 7,345,275 | B2 * | 3/2008 | Amirav et al. | 250/282 |
| 2005/0014286 | A1 * | 1/2005 | Furuki et al. | 436/514 |

FOREIGN PATENT DOCUMENTS

IL 176724 6/2006

* cited by examiner

*Primary Examiner*—David A. Vanore
(74) *Attorney, Agent, or Firm*—J. Harold Nissen; Lackenbach Siegel, LLP (57) ABSTRACT

There is provided a pulsed flow modulation gas chromatograph mass spectrometer with supersonic molecular beams apparatus and method for improved sample analysis. The apparatus includes a gas chromatograph with an injector for the analysis of sample compounds, a first analytical column in the gas chromatograph, a sample storage, a gas pulse generator, a pressure generator, a conduit for transferring the sample compounds into a second analytical column having a different polarity than the polarity of the first analytical column, a second gas pulse generator, a transfer line for transferring the sample compounds into a supersonic nozzle, a member for adding a makeup gas to the output gas flow of the second analytical column before the supersonic nozzle, an element for reducing the flow rate of the added makeup gas, a supersonic nozzle for the expansion of the sample with the combined second analytical column and added makeup gas, a fly-through electron ionization ion source, a mass analyzer, an ion detector for the detection of the ions of the sample compounds after their mass analysis, a data processor and presenter, and a repeater for repeating the cycle of the first gas pulse of relatively high flow rate followed by the second gas pulse of intermediate flow rate.

17 Claims, 2 Drawing Sheets

PULSED FLOW MODULATION GAS CHROMATOGRAPHY MASS SPECTROMETRY WITH SUPERSONIC MOLECULAR BEAMS METHOD AND APPARATUS

FIELD OF THE INVENTION

The present invention relates to a pulsed flow modulation gas chromatography mass spectrometry with supersonic molecular beams method and apparatus for improved sample analysis.

BACKGROUND OF THE INVENTION

Gas chromatography (GC) is a central analytical technique that serves a broad range of applications. In GC the sample is typically injected in a mixture with a few or many other matrix compounds, and separated in time by the GC column before its detection and quantitative determination by the GC detector. As a result, the GC separation capability is defined as one of its most important (prime) capabilities. Currently, most GC analyses are performed with a 30 m long non-polar capillary column with 0.25 mm ID, operated with 1 ml/min carrier gas flow rate, and the separation is predominantly based on the sample volatility, so that the elution times follow the boiling temperatures (order of volatility) of the eluting sample compounds. While the most widely used GC detector is the flame ionization detector (FID), the most important GC detector is clearly the mass spectrometer. The combination of gas chromatography and mass spectrometry (GC-MS) is a known powerful technology since GC-MS, unlike GC-FID, can also be used for sample identification, and it excels in mass selective detection of low level compounds in complex matrices. For a variety of petrochemical, food and other complex samples the GC separation is insufficient, due to lack of peak capacity and limited separation capability, and mass spectral identification is often hampered by extensive co-elution of several compounds that prohibit appropriate identification and quantitative determination. In order to improve the GC separation, comprehensive two-dimensional gas chromatography (GCxGC) was pioneered by Phillips and Liu [U.S. Pat. Nos. 5,135,549 and 5,196,039] and later on was further developed by Phillips and co-workers and many other investigators. GCxGC is based on comprehensive two dimensional GC separation, so that the full sample is first separated according to its volatility (boiling point) on typically a non-polar standard column and then in repeated cycles, the eluting compounds are focused (usually cryo focused) in space and pulsed injected into a second short semi polar or polar column for their second dimension separation according to the sample compounds polarity. GCxGC sample compounds that co-elute from the first analytical column typically have similar boiling points. Upon their pulsed injection into a second short column with polar separation film, those compounds that are chemically polar have stronger interactions with the second column adsorption film, are adsorbed for a longer period of time and thus the second column order of elution follows the sample order of polarity. GCxGC recently became a popular research area and it is well described in a few review articles such as J. Dalluge, J. Beens and U. A. T. Brinkman, J. Chromatogr. A. 1000, 69-108 (2003). GCxGC provides the following main advantages: a) Improved GC separation by a factor of about 5 to 20; b) Improved sensitivity by a factor of about 2-7 in view of 4 to 50 times narrower GC peaks; c) Reduced matrix interference in view of the improved GC separation, and d) Provision of additional sample polarity and group type information according to its second column order of elution.

The main added method and hardware element in GCxGC versus GC is the sample modulator. In GCxGC, the sample compounds which elute from the first column, are focused in space and pulse injected into a second short column for their second dimension separation. The sample focusing and pulsed injection into the second column is performed with a device called a sample modulator or modulator in short. The modulator determines the efficiency, performance, reliability and added cost of GCxGC and is hence considered the most important element in GCxGC technology. Several distinctive designs of GCxGC modulators were developed and some are commercially available. Currently, thermal modulators, which are based on sample cryogenic focusing (cryo-focusing), are most abundant and widely used as they provide the best GCxGC resolution through narrowest second GCxGC column injection time width. All the thermal modulators, however, are complex and costly devices, further consuming large amounts of $CO_2$ gas or liquid nitrogen, in the order of three large $CO_2$ cylinders per day or 80-100 liters of liquid nitrogen per day. As a result, despite the superior GCxGC performance over standard GC, its use and applicability are limited, in view of the cost and complexity of GCxGC thermal modulators and their high gas consumption.

While GCxGC was proven to be a powerful technique for improved separation of complex mixtures, most of the research was performed with GCxGC-FID and not with GCxGC-MS. Whenever sample identification and/or confirmation are required, however, the use of mass spectrometry for detection is mandatory. Since GCxGC with the common thermal modulators generates narrow chromatographic peaks with peak width that could be below 0.1 s, GCxGC requires the fast scanning speed of time of flight (TOF) mass spectrometers. GC-TOF-MS is, however, expensive and not as robust as standard quadruple GC-MS, and thus, GCxGC-TOF-MS is not frequently used. In view of the high cost and complexity of GCxGC-TOF-MS, GCxGC with quadruple MS was successfully explored and proved to be a valuable approach, although faster scan speed is still a highly desirable feature.

As a result of the above, GCxGC-MS suffers from several problems that need to be solved in order to make it a generally accepted useful analytical tool:

1. There is a need to solve the problem of adequate scan speed for quadruple MS, in order to enable the proper combination of GCxGC with the robust and low cost range of quadruple MS (or ion trap). Modern quadruple GC-MS are characterized by improved scan speed of >8,000 amu/s that can be >20 Hz in the 50-450 amu mass range.
2. Currently samples are identified mostly via the use of 70 eV EI libraries. However, sample identification with libraries is limited since most of the organic compounds are not included in any library. The identification of unknown compounds can be further confronted by frequent absence (or weakness) of the molecular ion.
3. The problem of frequently absent or weak molecular ions is further exacerbated with TOF-MS for two main reasons: a) TOF-MS uses a multi channel ion detector and do not employ a conversion dynode for reasons of time resolution, so that in GC-TOF-MS, the molecular ion and other high mass ions are relatively suppressed in comparison with quadruple GC-MS that uses conversion dynode based ion detectors, and b) while it is recognized that narrow GCxGC peaks require fast scan speed, it is similarly true although generally neglected that narrow GCxGC peaks similarly require fast ion source response time. Semi-volatile and low volatility samples, however, tend to have lengthy intra ion source adsorption-thermal-desorption cycles, which induce peak broadening and tailing. Thus, the need for 10 times faster ion source response time, also requires ~70° C. hotter ion source temperature. This increased ion source temperature significantly (exponentially) reduces the relative abundance of the molecular ion and impede sample identification both with and without the library.

4. The known Achilles Hill of GC is its limited range of thermally stable and volatile compounds amenable for analysis. This problem of limited range of compounds amenable for analysis is further exacerbated in GCxGC-MS due to the need to use significantly increased ion source temperature, which promote excessive intra ion source decomposition of thermally labile compounds.

5. Thermal modulators are complex, expensive and require large amount of cryogenic gases.

Thus, there is a long felt need to provide a quadrupole (or ion trap) based GCxGC-MS that will effectively operate without requiring costly cryogenic gases and that will provide trustworthy molecular ion combined with library searchable mass spectra for an extended range of thermally labile and low volatility samples.

Around the year 2000, Seeley and co-workers, (J. V. Seeley, F. Kramp and C. J. Hicks, Anal. Chem. 72, 4346-4352 (2000)), developed and presented a new approach of flow modulation GCxGC as an alternative to thermal modulation GCxGC and later on they further characterized and explored this flow modulation method. According to Seeley's flow modulation method, the output of the first GCxGC analytical column is directed to a storage transfer line column and then injected with typically 20 times higher flow rate (20 ml/min) into the second GCxGC column, while the first analytical column output flow is directed to a second parallel storage transfer line column. After a few seconds the 20 times higher flow rate is modulated and directed to the second storage transfer line column for the injection of its content into the second GCxGC column and such a cycle is repeated for affecting comprehensive GCxGC analysis. Flow modulation is a relatively simple and low cost method for GCxGC modulation, but it suffers from two new problems:

A) Flow modulation GCxGC is characterized by significantly reduced GCxGC separation due to the use of high column flow rate of 20 ml/min in combination of large bore capillary column (such as with 0.32 mm I.D.). The combination of 3 meter 0.32 mm I.D. column operated with 20 ml/min, provides about 20 times less number of theoretical separation plates in comparison with the typically used 1 meter long 0.1 mm I.D. micro-bore capillary columns. This reduced number of separation plates can be translated into 4.5 times poorer GCxGC separation, which serves as a major deterrent from flow modulation GCxGC.

B) Flow modulation requires compatibility with a high second column flow rate of about 20 ml/min, which makes it incompatible with standard GC-MS instrumentation that are designed to work with 1 ml/min column flow rate. Although some GC-MS systems can accept a few ml/min column flow rates, their ion source response is significantly lower with higher column flow rates due to increased intra ion source space charge.

The combination of A and B above and the need to address the problem of limited scan speed of standard mass analyzers (quadrupole and ion trap) explains why despite its cost and maintenance advantages, flow modulation GCxGC was not combined with standard GC-MS.

In the last decade there has been developed and explored the performance capabilities of a new type of GC-MS, based on the use of a supersonic molecular beam (SMB). SMB was used for interfacing the GC to the MS and as a medium for ionization of sample compounds while vibrationally cold in the SMB, either by electron ionization (EI) or by hyperthermal surface ionization (HSI). SMB (with helium as carrier gas) is characterized by intra-molecular vibrational supercooling of its seeded sample molecules due to relatively low collision energies of sample compounds and carrier gas species during the supersonic expansion. Consequently, the molecular ion ($M^+$) intensity is enhanced in EI with SMB (also named "cold EI") and it is practically always exhibited, yet the library searchable fragment ions are retained. In addition, isomer mass spectral information is significantly amplified and accurate isotope abundance information is revealed (which also provide unique elemental formula information) without any self-chemical ionization interferences. The SMB interface is compatible with high carrier gas flow rate of about 90 ml/min through the use of differential pumping in an added vacuum chamber. Furthermore, SMB is characterized by the fly-through motion of the sample compounds in the ion source and by vacuum background filtration, and as a result, the SMB fly-through ion source is characterized by tailing-free ultra-fast ion source response time regardless the sample volatility, which is an important feature for GCxGC-MS in view of its need to comply with the tailing free analysis demands of sub one second GC peaks. Thus, the use of GC-MS with SMB provides a range of advantages which offset its higher price and added complexity in view of the need for added vacuum chamber and pump.

While evaluating the flow modulation method, it is realized that an important yet not fully appreciated feature of flow modulation is that the minimal GCxGC peak width (injection time) is the collection time (typically 4 sec.) divided by the second column to first column flow rate ratio (typically 20). Thus, flow modulation provides GCxGC peak width that can be controlled, including in the convenient range of 0.2-0.3 s in order to make it amenable for the scan speed of quadruple or ion trap GC-MS. As a result, it was surprisingly found that the previously considered adverse flow modulation feature of increased peak width, hence lost GCxGC separation resolution has an important merit in enabling the use of quadruple mass spectrometry (and other low scan speed MS such as ion trap and magnetic sector) despite its limited scan speed. On the other hand, in order to benefit from this feature, it is required to address the standard GC-MS flow rate limitation of 1 ml/min and enable the use of 20 ml/min carrier gas flow rate without any sacrifice in sensitivity. The solution for this demanding feature is the use of GC-MS with supersonic molecular beam according to the present application that can accept any column flow rate up to 100 ml/min without any adverse effect on its sensitivity.

Consequently, in flow modulation GCxGC-MS with SMB, the problem of limited quadruple mass analyzer scan speed is solved via flow modulation injection broadening of the eluting peaks, which as a result of their increased peak width require less mass spectral scans per unit time. In addition, the molecular ion abundance is significantly enhanced through the use of SMB, ultra-fast ion source response time is provided with SMB regardless of the sample volatility, and the flow modulation requirement of compatibility with 20 ml/min column flow rate is easily addressed by the SMB differential pumping.

Flow modulation seems deceivingly simple but it was found that it possesses several limitations and disadvantages which hampers its effective use including:

1. The Seeley flow modulation "arrangement" is delicate. It is composed of four T union connectors plus six "small"

transfer line columns in addition to the GCxGC two main analytical columns, and this complete structure has to be mounted on a piece of mesh introduced into the limited space of the GC oven;
2. The flow modulation structure contains four delicate low thermal mass T union connectors that are the subject of frequent leaks;
3. The Seeley flow modulation GCxGC method development is relatively complicated, as it is based on narrow range of flow rates and flow impedance transfer line columns. As a result, once the flow modulation is based around 1 ml/min first column flow rate, it is inconvenient and not practical to change this flow rate;
4. Flow modulation GCxGC must use constant pressure and is incompatible with the GC industry standard mode of constant flow operation unless an additional electronic flow control is used;
5. Flow modulation GCxGC is characterized by reduced second dimension GC separation. The same desirable feature of relatively broad GCxGC peaks implies lost GCxGC resolution. In addition, the high second column flow rate also implies reduced number of second column separation plates and peak capacity, and
6. The Seeley flow modulation method shares with thermal modulation GCxGC the problem of ghost peaks (also named turn around peaks) in the second analytical column.

DESCRIPTION OF THE INVENTION

It is therefore a broad object of the present invention to provide a method and apparatus for improved gas chromatography mass spectrometry with supersonic molecular beams and particularly GCxGC-MS with SMB that it operated with quadruple or ion trap mass analyzers.

In accordance with the present invention there is therefore provided a pulsed flow modulation gas chromatography mass spectrometry with supersonic molecular beams method for improved sample analysis, comprising the steps of injecting a sample into a gas chromatograph, separating said sample compounds in the gas chromatograph by a first analytical column, eluting the sample from said first analytical column into a storage transfer column, passing a first gas pulse, of a relatively high flow rate carrier gas, through a gas line into a gas line connector also connecting the first analytical column and said storage transfer column, forming an increased pressure at the gas line connector by said high flow rate carrier gas pulse, to temporarily stop sample elution from said first analytical column, transferring the sample compounds in the storage transfer column with said high flow rate carrier gas pulse, into a second analytical column of a different polarity than the polarity of said first analytical column, providing a second gas pulse of intermediate carrier gas flow rate, of a duration longer than the duration of said first gas pulse for the separation in time of the sample compounds in said second analytical column, adjusting the time of said first gas pulse, second gas pulse and the ratio of second analytical column flow rate to first analytical column flow rate, to provide second analytical column chromatographic peak widths that are sufficiently broad to enable compatibility with a scanning speed of a mass spectrometer, adding makeup gas to the output gas flow of the second analytical column, reducing the flow rate of said added makeup gas to compensate for the increased second column flow rate, transferring said sample compounds via a heated transfer line into a supersonic nozzle, expanding said sample and combined second column and added make up gases from said supersonic nozzle for the formation of vibrationally cold sample compounds in a supersonic molecular beam, ionizing said sample compounds by electrons in a fly through ion source while they are contained in said supersonic molecular beam, analyzing the ions formed from said sample compounds in said supersonic molecular beam in a mass analyzer of a mass spectrometer, detecting said ions of said sample compounds after their mass analysis with an ion detector, processing the data obtained from the mass spectrometer after ion detection for identifying and/or quantifying the chemical content of said sample, and repeating the cycle of said first pulse of relatively high flow rate followed by said longer, second pulse of intermediate flow rate, in a repetitive fashion.

The invention further provides a pulsed flow modulation gas chromatograph mass spectrometer with supersonic molecular beams apparatus for improved sample analysis, comprising a gas chromatograph with gas chromatograph injector for the analysis of sample compounds, a first analytical column in said gas chromatograph for the separation in-time of said sample compounds, sample storage means for temporarily storing said sample compounds after their elution from said first analytical column, a gas pulse generator for the generation of a high flow rate carrier gas pulse to be transferred through a gas line into a gas line connector also connecting the first analytical column and said sample storage means, pressure forming means for creating an increased pressure at said gas line connector by said high flow rate carrier gas pulse, to temporarily stop sample elution from said first analytical column, a conduit for transferring the sample compounds in said sample storage means with said pulsed high flow rate carrier gas, into a second analytical column, said second analytical column having a different polarity than the polarity of said first analytical column; a second gas pulse generator for generating a second gas pulse of a longer duration, for the separation of the sample compounds in said second analytical column, a transfer line for transferring the sample compounds eluting from the second analytical column into a supersonic nozzle, means for adding a makeup gas to the output gas flow of the second analytical column before said supersonic nozzle, means for reducing the flow rate of said added makeup gas to compensate for the increased second column flow rate, a supersonic nozzle for the expansion of said sample with the combined second analytical column and added makeup gas, for the formation of vibrationally cold sample compounds in a supersonic molecular beam, fly through electron ionization ion source for the ionization of said sample compounds while they are contained in said supersonic molecular beam, mass analyzer for analyzing the ions formed from said sample compounds in said supersonic molecular beam in a mass spectrometer, ion detector for the detection of said ions of said sample compounds after their mass analysis, means for data processing and presentation of the mass spectral data for identifying and/or quantifying the chemical content of said sample, and means for repeating the cycle of said first gas pulse of relatively high flow rate followed by said longer, second gas pulse of intermediate flow rate, in a repetitive fashion.

BRIEF DESCRIPTION OF THE DRAWINGS

The invention will now be described in connection with certain preferred embodiments with reference to the following illustrative figures, so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DETAILED DESCRIPTION OF THE INVENTION

Figure 1:
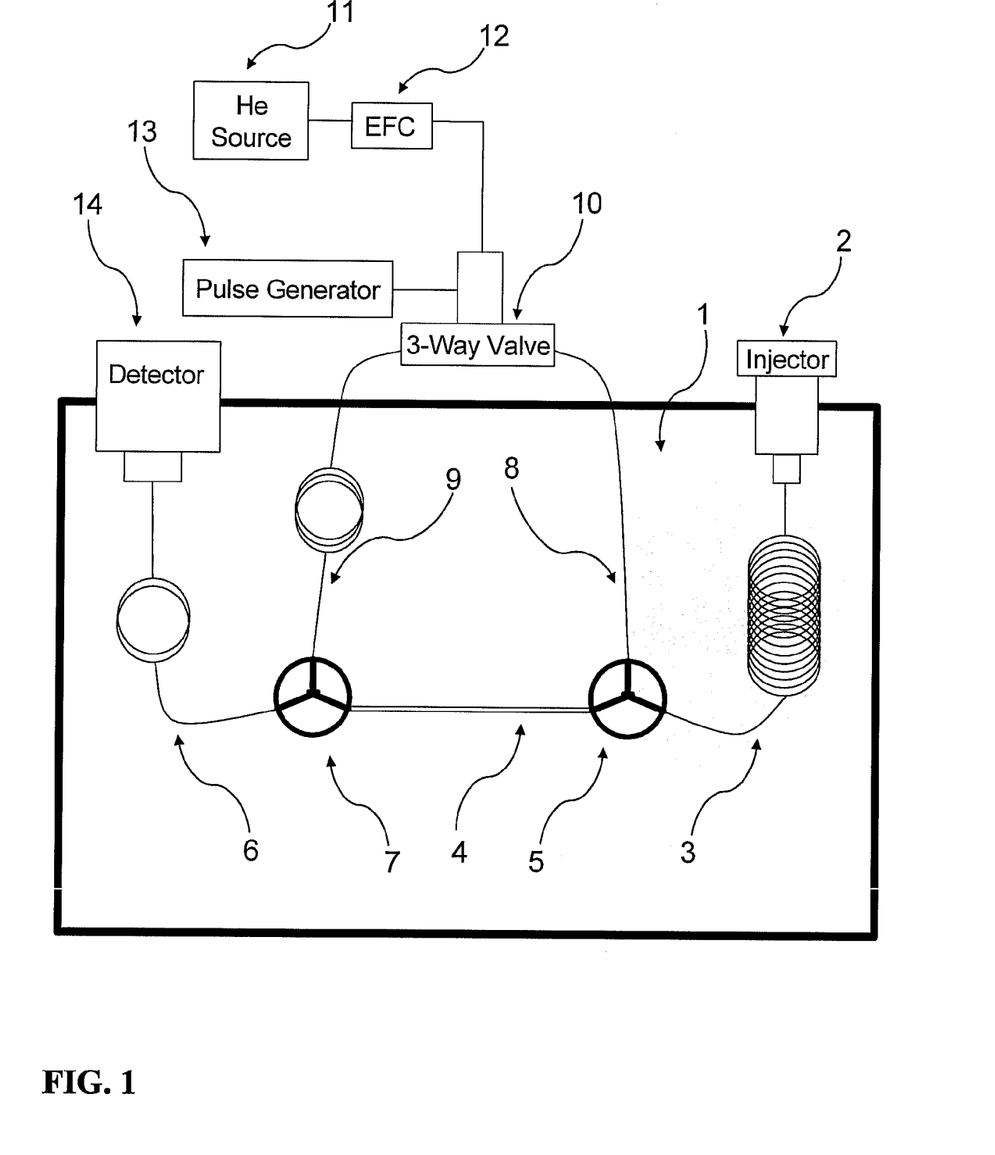
FIG. 1 is a schematic diagram illustrating a pulsed flow modulation device, according to the present invention.

Illustrated in FIG. 1 is a flow modulation device according to the present invention. The device and method are referred to as "pulsed flow modulation" in distinction to other flow modulation methods and devices. Sample compounds are injected into a CG 1 by an injector 2 and directed to a first analytical column 3. The sample compounds elute from the first GC analytical column 3 into a storage transfer line column 4 through a first connector 5, e.g., a Y connector. The storage transfer line column 4 is connected to a second GCxGC analytical column 6 via a second connector 7, e.g., a Y connector. The two Y connectors are respectively further connected via a first gas transfer line 8 and a second gas transfer line 9 to a three-way solenoid valve 10 which controls the flow of, typically helium, from a helium source 11 through an electronic flow (and/or pressure) control 12. The solenoid valve 10 can modulate the direction of gas delivery through the control of a pulse generator or computer 13. The output of the second analytical column 6 is detected by the GC detector 14 or transferred through a heated transfer line to a supersonic nozzle for mass analysis with SMB according to the present invention. At a given time after the storage transfer line column 4 is full or almost full, a pulse of about 28 ml/min helium, for about 0.2 sec., is directed by the solenoid valve 10 through the gas transfer line 8 into the first Y connector 5, and the sample compounds that previously eluted from the analytical column 3 into the storage transfer line column 4, are quickly flushed into the second analytical column 6 while temporarily stopping the first analytical column 3 flow, hence, stopping any sample elution from column 3. After this short gas flow pulse, the three-way solenoid valve 10 changes its direction for a few seconds (typically 1 to 10 sec.) and the flow in the first gas transfer line 8 stops while the flow in the second gas transfer line 9 commences at a lower flow rate, since gas transfer line 9 has a higher flow impedance, because it is typically longer or has a smaller internal diameter than line 8. This lower flow rate through gas transfer line 9 enables the separation in time and elution of the sample compounds in the second analytical column 6, while the sample which elutes from the first analytical column 3, is stored in the storage transfer line column 4. The flow rate in the second analytical column 6 is typically in the 15 to 20 ml/min flow rate range. The flow modulation process is repeated periodically every few, e.g., 4 seconds, controlled by the pulse generator or computer 13 to affect comprehensive GCxGC separation.

The polarity of the adsorption film of the second analytical column 6 is different than that of the first analytical column 3, in order to induce second dimension GC column separation for compounds that co-eluted from the first column. Typically the first column 3 has a non-polar adsorption film (such as polydimethylsiloxane) while the second column is characterized by a semi-polar or polar adsorption film (such as with 50% phenyl group), but this order could be reversed. Transfer lines are substantially equivalent to columns with minimal or zero absorption film thickness.

The main feature of the pulsed flow modulation is that the short, high flow rate pulse, which flushes the sample from the storage transfer line 4 to the second analytical column 6, also simultaneously stops the elution of sample compounds from the first analytical column 3. Since the pulse flow rate through gas transfer line 8 is high, i.e., higher than through gas transfer line 9, it creates a higher pressure at the first Y connector 5, which not only stops the first analytical column 3 flow rate, but could also revert the flow into first analytical column 3 from its output end. Such column flow stopping or reversal, however, is only temporary, for about or less than 5% of the time, thus not significantly affecting the gas chromatography separation of the first column. Without the preclusion of sample elution from the first column during its injection to the second column, the GCxGC baseline will be "contaminated" and the end result will be a combination of standard GC and GCxGC chromatograms, which will hamper any quantitative analysis. The fact that a pressure pulse with lower pressure than the column head pressure is sufficient to temporarily stop the column flow is surprising. It can be understood in view of the fact that the average column pressure is increased by this pulse, and thus, for a short (<1 sec.) time the first analytical column 3 accepts carrier gas from both its input and output ends. As a result, the injection flow pulse must provide increased pressure that will be sufficient only for temporarily halting sample elution from the first column. The magnitude of required increased pressure can be calculated or obtained experimentally. Since the pressure between analytical columns 3 and 6 is increased during the injection pulse, even if the pressure is lower than the analytical column 3 head pressure at the injector, the flow output from analytical column 3 can be temporarily fully stopped.

This combination of sample injection into the second GCxGC analytical column 6 and stopping of sample elution from the first GCxGC analytical column 3 can be achieved in a few other similar, but not identical ways. In FIG. 1 there are used two different transfer lines, first transfer line 8 with low flow impedance and a second transfer line 9 with higher flow impedance. As a result, while using the same head pressure at the solenoid valve 10, the pressure at the first Y connector 5 was higher during the pulsed injection than the pressure at both Y connectors 5 and 7 during the second longer pulse, due to extended pressure gradient on the longer and higher flow impedance of the second transfer line 9. These pressure differences, however, can be obtained in other ways such as by the use of two separate electronic flow or pressure controls. Thus, the first transfer line for example can be connected into a two-way solenoid valve instead of a three-way solenoid valve, as in FIG. 1. The simpler two-way (on-off) solenoid valve can be controlled by a pulse generator or computer and accepts helium gas from a separate helium gas source through a separate electronic flow and pressure control (EFC). Similarly, the second transfer line can be connected into a second helium gas source with flow rate (and/or pressure) that is controlled by a second separate EFC. The helium gas source can be different or conveniently the same for both gas transfer lines and EFC. The main difference between the pulsed flow modulation according FIG. 1 and this variation, is that two solenoid valves and EFC are used instead of a single three-way valve and one EFC. This arrangement provides greater flexibility and easier flow programming of the second GCxGC analytical column to suppress ghost peaks and it enables the use of identical transfer lines 8 and 9 (or broader range of such transfer lines). However, the added flexibility requires added hardware elements that increase the cost of the pulsed flow modulation device.

While the above description pertains to the pulsed flow modulation, in general, this method was successfully tested with a model 6890 GC (Agilent Technologies, Wilmington, Del., U.S.A.) and with a Varian model 1200 GC-MS that was modified to work with a home made SMB interface and its fly-through ion source (also named 1200-SMB) as descried in detail in A. B. Fialkov, U. Steiner, L. Jones and A. Amirav, Int. J. Mass. Spectrom. 251, 47-58 (2006). In the experiments, samples were typically injected into a standard 15 m long 0.25 mm ID column with 0.25μ DB-5 ms film. This analytical column 3 served for the first dimension GCxGC separation according to volatility. Analytical column 3 output was eluted through a Y flow connector splitter 5 (Y vu connector, Restek, Bellefonte, Pa. U.S.A. or a standard 1/16" brass compression fitting) and it was directed to a low flow impedance storage capillary transfer line column 4 (50 cm, 0.53 mm ID deactivated fused silica transfer line column). Pulsed flow modulation was obtained by means of a three-way solenoid valve 10. This valve was fed with helium by the electronic flow control 12 and its open output direction was controlled by a standard pulse generator 13 controlling the valve driver. Typical He flow rate through the solenoid valve was either 28 ml/min for 0.2 sec. into the 40 cm fused silica capillary transfer line 8 with 0.32 mm ID, or 20 ml/min for 3.8 sec. into a 40 cm fused silica capillary transfer line 9 with 0.25 mm ID, both obtained with the same helium pressure of 1 Atm (15 PSIG). The 20 ml/min helium flow rate served to elute the sample from the second GCxGC polar second analytical column 6 (4 m 0.25 mm ID with 0.25μ RTX50 semi polar film).

Use of capillary tubing with increased length or smaller diameter is a convenient way to increase the flow impedance of the carrier gas. Thus, with such two different gas tubes, one can conveniently use a one three-way solenoid valve that is fed from a one helium gas supply, yet to obtain different carrier gas flow rates and pressures at the end of these capillary gas tubes. However, the flow impedances can also be changed and controlled by other alternative means such as flow impedance frits that are known in the art and widely used.

In experiments conducted, there has been used a storage transfer line column 4, e.g. a 50 cm long 0.53 mm I.D. deactivated fused silica capillary transfer line column. The use of such capillary transfer line represents a convenient choice of sufficient volume for the temporary storage of sample compounds. However, alternative sample storage means can be used, including an inert union with adequate volume and/or micro fluidic passageways (with low thermal mass) made in any structure. Such a micro fluidic passageway can include spiral internal channels to control the storage channel/column, volume. These types of structures will be referred to herein as "storage columns". Similarly, while in some experiments we used fused silica inert Y connectors, these connectors were found to be highly delicate and fragile. Eventually, it was found that simple 1/16" brass compression fittings could be used while placing the analytical columns 1-2 cm inside the 0.53 mm I.D. storage transfer line. This arrangement of the gas path is simpler, cheaper, and more robust. In addition, this arrangement was also without any dead volume due to dynamic gas sweeping of the columns outputs. It required slightly longer storage transfer line 4 to enable pure helium at its end to be compressed into the gas transfer line 9 during the short high pressure pulse before the arrival of the sample in order to preserve sample path inertness.

Flow modulation typically requires the use of a second analytical GCxGC column 6 with a larger internal diameter for it reduced flow impedance compatibility with the required relatively high second column flow rate. Helium is used as the preferred carrier gas but hydrogen, nitrogen and combinations thereof, can also be used. The pulsed modulation helium flow rate was a parameter that could be changed as needed to control the minimal GCxGC peak width, so that it would be amenable for the scan speed of quadruple MS. When 16 ml/min were used with 1 ml/min analytical column 3 flow rate every 4 sec. GCxGC period, the second analytical column 6 minimal peak width was $4 \times 1/16 = 0.25$ sec. due to the pulsed flow modulation injection broadening. The various flow modulation components (two Y connectors and storage capillary) were mounted on a crude mesh that was placed inside the GC oven, while the solenoid valve and its control remained outside the heated GC oven. The flow modulation device is relatively simple, inexpensive to construct and easily assembled.

Figure 2:
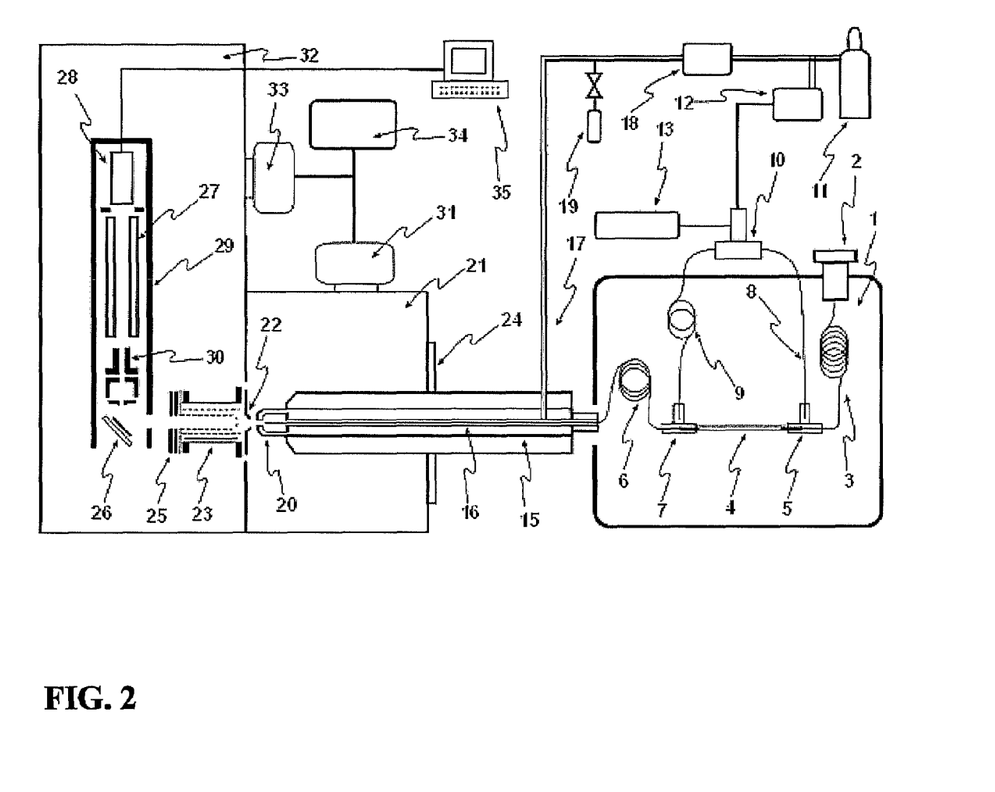
FIG. 2 is a schematic diagram illustrating the apparatus of the pulsed flow modulation gas chromatograph mass spectrometer with supersonic molecular beams according to the present invention.

In FIG. 2 a schematic diagram illustrating the full apparatus of the pulsed flow modulation gas chromatograph mass spectrometer with supersonic molecular beams according to the present invention is shown. In FIG. 2, elements 1-13 constitute and describe the pulsed flow modulator and are the same as in FIG. 1 but the GC detector 14 is now a mass spectrometer with supersonic molecular beams (SMB). The sample compounds, which elute from the second analytical column 6, are directed to a supersonic nozzle via a transfer line 15, which is separately heated by heater 16. The output gas flow of column 6 is mixed with make up gas, typically pure helium which is provided through make up gas line 17, whose flow rate is separately controlled by electronic flow (or pressure) controller (EFC) 18, to compensate for the added GCxGC second column flow rate and provide near atmospheric pressure behind a supersonic nozzle. A mass spectrometer calibration and tuning compound (such as perfluorotributylamine) can be added to the make up gas line through its container and computer controlled solenoid valve 19. The sample in transfer line 15 before (upstream of) the supersonic nozzle 20, is typically transferred in the same second separation column 6. The helium seeded sample compounds expand from the supersonic nozzle 20 into a first vacuum chamber 21, while being vibrationally cooled, skimmed by a skimmer 22, collimated into a seeded supersonic molecular beam that contain vibrationally cold sample compounds which are ionized by electron impact in a fly-through ion source 23. The transfer line is located on a vacuum sealed XYZ table 24 for its optimal positioning in front of the skimmer 22. After ionization the ions of the sample compounds are focused by ion lens system 25 which can also act as vacuum background filtration element through slight positive biasing of one of its lens elements. The sample ion beam output of ion source 23 and lens system 25 is typically reflected 90 degrees by an ion mirror 26 and introduced into a quadrupole mass analyzer 27 for their mass analysis followed by ion detection in an ion detector 28. The mass analyzer scanning speed is adjusted to comply with the expected GCxGC peak width, which is controlled by the pulsed flow modulation. The mass analyzer is typically located in mass analyzer house 29 that further contain mass analyzer ion lens system 30. The supersonic nozzle 20 output gas flow rate is discharged into a differentially pumped vacuum chamber 21, that is pumped by turbo molecular pump 31, while the fly through EI ion source 23, mass analyzer 27 and its ion detector 28 are located in a high vacuum chamber 32 that is separately pumped by turbo molecular pump 33. Both turbo molecular pumps are backed by a single rotary pump 34. Typical pumping speed of the turbo molecular pumps is 250 L/s and that or the rotary pump is 100 L/min. A single split turbo molecular pump can replace the two separate turbo molecular pumps if such a pump has adequate helium inter-stage compression ratio. The high vacuum turbo pump 33 can also be backed by the nozzle vacuum chamber 21, and in that case, the rotary pump 34 will back up and pump only the nozzle chamber turbo molecular pump 31. The signal is processed by a computer with data analysis software 35 and the computer is also equipped with system control software.

The method and apparatus according to the present invention provides improved comprehensive GCxGC-MS with SMB. It is characterized by several advantages of the pulsed flow modulation device itself and as a full apparatus of pulsed flow modulation GCxGC-MS with SMB. Among the advantages of the pulsed flow modulation (PFM) method and device the following are listed below:

1. Pulsed flow modulation according to the present invention, is the simplest, easiest to use and is an inexpensive GCxGC modulation method and device;
2. In comparison with currently available thermal modulation, it eliminates the GC maintenance cost and complexity involved in the need to use large amounts of liquid nitrogen or $CO_2$ and frequent cylinder replacement and storage. The added helium modulation gas is subtracted from the SMB helium make up gas; hence the pulsed flow modulation practically does not require any added gas, and
3. In comparison with other flow modulation methods and devices, it does not make use of more than half of the components, is simpler to mount and maintain in the GC, more flexible in GCxGC method development and can work with a broader range of flow rates. In addition, the stored sample compounds after their elution from the first column, are not diluted with added carrier gas that directs them to the left or right storage columns.

Thus, while flow modulation, including the pulsed flow modulation reduce the theoretical GCxGC separation power in view of both its injection time broadening and high flow rate in the second GCxGC column, it provide all the standard known merits of GCxGC. As a result, pulsed flow modulation brings all the major GCxGC advantages into PFM-GCxGC-MS with SMB analysis including: a) Increased GC separation; b) improved sensitivity via narrower GC peaks; c) increased sensitivity via the reduction of matrix interference in the analysis of samples in complex matrices, and d) polarity and functional group (group type) sample information via the order of second column elution.

The method and apparatus of pulsed flow modulation gas chromatograph mass spectrometer with supersonic molecular beams is characterized by several unique features and advantages, including:

1. The injection time width is adjusted to be broad enough to enable GCxGC compatibility with the scan speed of slow mass analyzers such as quadrupole, ion trap or magnetic sector, which is against expectations, as it comes with a trade off of theoretical GCxGC separation which is its prime feature;
2. The need for high PFM second column flow rate compatibility of the vacuum system and ion source is enabled by the use of SMB interface and its differentially pumped fly through ion source;
3. The added SMB make up gas flow rate is reduced to compensate for the high $2^{nd}$ GCxGC column flow rate;
4. The combination of pulsed flow modulation and GC-MS with SMB with its high flow rate acceptance is uniquely compatible with convenient flow programming of the second GCxGC column, thereby eliminating the problem of ghost peaks (also named turn around peaks) of highly polar compounds that tend to elute at the next cycle in the second column;
5. The SMB major capability of extended range of compounds amenable for analysis is partially sacrificed for having PFM-GCxGC capability due to the PFM limitation on the first column flow rate. While at first glance this trade off seems deterrent, considering the ability to use pulsed high flow rate injection in combination with short first GCxGC column and fully inert fly through ion source, this loss of extended range is not detrimental;
6. Ultra fast ion source response time is provided via the SMB-MS feature of vacuum background filtration in it zero field fly through ion source and ion optics. This is an unrecognized yet very important feature for GCxGC-MS. This ultra fast ion source response provides tailing free improved PFM-GCxGC separation of semi volatile and low volatility compounds;
7. The second GCxGC column uniquely ends at high pressure before (upstream of) the supersonic nozzle, instead of at vacuum inside standard EI ion source in standard GCxGC-MS. This feature unexpectedly enables back-flush for significantly reduced analysis time. Thus, with PFM-GCxGC-MS with SMB, midpoint back-flush pressure is always positive, and it can be relatively high for short time back-flush without a need for adding a transfer line flow splitter that reduces the sensitivity and quantitation due to oven temperature dependence of its split ratio;
8. PFM-GCxGC is characterized by increased second column flow rate. It was unexpectedly found that as a result, it correspondingly increases sample capacity, measurement linear dynamic range and practical GCxGC separation due to improved second column separation of sample compounds from major matrix components. Thus, the same high flow rate that cannot be accepted by standard MS and that seemingly deteriorates the GCxGC separation by a factor of 4-5 is actually helping the separation "in the back door" via improved sample capacity;
9. The present method unexpectedly uniquely preserves the first column separation at the pulsed flow modulator storage transfer line and in its time compression injection into the second column. Thus, unlike with thermal modulation, with PFM one can perform faster GCxGC-MS with SMB separation without sacrificing first column separation, and
10. PFM-GCxGC-SMB-MS-MS provides ultimate selectivity in which each element contributes to the selectivity. MS-MS is very hard (not practical) to operate with TOF while the quadrupole mass analyzers scan speed limitation is uniquely resolved according to this application by increased GCxGC injection time with the PFM to enable the important added feature of MS-MS.

The combinations of these 10 features provide major overall improvement in the central performance aspects of GCxGC-MS, some of which are surprising and not immediately apparent, including:

A. Improved GCxGC-MS Separation.

At first glance it seems that the PFM-GCxGC-MS separation is highly inferior to that of thermal modulation GCxGC-MS since PFM uses wide bore second columns with very high column flow rates plus significantly increased injection time to broaden the injection in order to comply with the relatively low scan speed requirement of quadrupole mass analyzers. Thus, the theoretical PFM-GCxGC separation is about 4-5 times lower than of standard thermal modulation GCxGC. However, as surprising as it may seem, it is claimed that the practical separation of PFM-GCxGC-SMB-MS according to the present invention is in fact superior to that of standard thermal modulation GCxGC-TOF-MS for the following three main reasons:

A1. Elimination of intra ion source peak tailing. While thermal modulation can provide narrow initial GCxGC peaks and TOF-MS can provide adequate scan speed for their mass spectral detection, for many semi volatile compounds intra ion source peak tailing significantly deteriorates the practical GCxGC separation due to this peak tailing. An obvious standard remedy for this peak tailing is increased ion source temperature, and for the factor of 10 narrower GCxGC peaks in comparison with standard GC-MS, 70C hotter ion source temperatures are required in order to eliminate peak tailing. However, such increased ion source temperature comes with a severe penalty of exponentially reduced relative abundance of the molecular ion and as a result reduced sensitivity and library search ability hence sacrificed sample identification capability. In addition, thermally labile and other delicate sample compounds could significantly degrade in the hotter ion source. Thus, the fly-through ion source of SMB-MS with its tailing free ultra fast ion source response time provides improved practical GCxGC-MS separation, particularly for semi volatile, low volatility and thermally labile sample compounds.

A2. Vastly increased sample capacity and linear dynamic range. Another surprising positive feature of the pulsed flow modulation GCxGC-MS with SMB is that the sample capacity of the second GCxGC column is increased by about a factor of 100 in comparison with thermal modulation and microbore columns with 100 micron ID. Sample capacity relates to the sorption film volume of a separation plate. Since increased carrier gas beyond optimal flow rate linearly increases the plate height, 20 ml/min implies 20 times higher sample capacity, which combined with the use of 3.2 times bigger second column ID means that sample capacity is increased by a factor of over 100 times. In addition, the important feature of measurement linear dynamic range is similarly correspondingly increased by a factor of over 100 times. However, the most important yet surprising aspect of this use of high column flow rate with SMB is that the practical PFM-GCxGC-MS with SMB separation is also improved since peak fronting of abundant matrix that usually overload the thermal modulation second GCxGC column is now fully avoided. Thus, the separation of trace level samples in complex matrices is actually improved due to better separation from the matrix through the same PFM related change of column diameter and flow rate that reduces the theoretical separation.

A3. Improved mass spectrometer separation due to the enhancement of the molecular ion. The separation of the PFM-GCxGC-SMB-MS is that of the full system and not only of its PFM-GCxGC. Thus, the separation power of the MS actually supplements and complements that of the GCxGC. It is well known that the selectivity hence separation of the mass spectrometer of sample compounds from matrix interferences is far superior on the molecular ion than on any other fragment ion. Thus, the feature of SMB of enhanced molecular ion actually significantly improves the separation power of PFM-GCxGC-SMB-MS. This increased separation is in contrast to the use of TOF-MS with increased ion source temperature which results in significant reduction of the molecular ion relative abundance, hence reduced separation power of the MS.

Thus, in view of the above thee reasons the separation of the PFM-GCxGC-SMB-MS is actually improved in practical applications in comparison with other GCxGC-MS methods.

B. High flow rate compatibility and superior sensitivity. GC-MS with SMB is characterized by high flow rate compatibility, far more than any other GC-MS. In fact, GC-MS with SMB can accept splitless even 90 ml/min while standard GC-MS is designed to accept only one ml/min helium flow rate. Some standard GC-MS are advertised as capable of accepting higher flow rates such as 8 ml/min. However, any increase of the column flow rate beyond about 1 ml/min significantly reduces the sample signal in standard GC-MS due to adverse intra ion source space charge effects. Only GC-MS with SMB is equipped with differential pumping before the ion source and has a constant expansion flow rate regardless the GC column flow rate. Thus, the increased second PFM GCxGC column flow rate is uniquely fully compensated by similar reduction in the added helium make up gas flow rate, hence the nozzle flow rate is constant and unchanged and as a result the sensitivity is uniquely unaffected by any increase or decrease in the second column flow rate.

C. Faster GCxGC-SMB-MS analysis. GCxGC-MS is usually slower than GC-MS since with thermal modulation there is a need to preserve the separation of the first column and thus to broaden the first column peak so that over three GCxGC cycles will be included in the time of first column GC peaks. Thus, a very slow temperature program is used to broaden the first column GC peaks and as a result GCxGC analysis could take over an hour and even two hours. In contrast, PFM is uniquely characterized by the preservation of first column partial or full separation in the storage transfer line and as a result in the pulsed injection of the content of the storage transfer line which preserves the separation and only compresses it in time. Thus, with PFM faster temperature program rate can be used for faster PFM-GCxGC-SMB-MS analysis.

D. Ultimate selectivity for improved sample analysis in complex matrices. While the feature of increased column capacity as mentioned above helps to improve the separation of sample from its matrix, two additional features help to improve the method selectivity. The feature of enhanced molecular ion improves the selectivity and separation power of the mass spectrometer and the ability to use quadrupole mass spectrometers despite their limited scan speed opens the door for the use of triple quadrupole based MS-MS. MS-MS is a known method for the provision of significantly improved selectivity and as a result sensitivity in the analysis of trace level samples in complex matrices. Thus, PFM-GCxGC-SMB-MS-MS can provide ultimate selectivity with its known benefits. While each of the three; PFM-GCxGC, SMB and MS-MS, contribute to the system selectivity, their combination is much more than a simple linear addition of their benefits since the user can translate each feature to another. For example, if the PFM-GCxGC or enhanced molecular ion with SMB provides sufficient selectivity, the mass spectral resolution of the MS-MS can be traded and via a small (factor of 2) loss of MS resolution an order of magnitude greater signal can be gained. Alternatively, extended selectivity can be used for relaxed requirements from the labor intensive and costly sample preparation. Another alternative is the use of short first column and faster temperature programming for obtaining faster analysis at the expense of selectivity or separation. Thus PFM-GCxGC-SMB-MS-MS can serve for improved sample identification and quantitation in the most complex matrices, such as petrochemical, crude oil, bio fluids and/or agricultural products. We believe that for the identification of pesticides and other target or unknown samples, PFM-GCxGC-SMB-MS is superior to GCxGC-TOF-MS.

While the above description is aimed at improved GCxGC-MS analysis through the use of the SMB interface and its fly through EI ion source, the pulsed flow modulation GCxGC-MS with SMB method and apparatus as described above can also be used for improved GC-MS with SMB analysis when the second GCxGC column such as analytical column 6 in FIG. 1 is replaced by a short, low volume deactivated capillary transfer line (with minimal separation film thickness or no separation film) that is connected directly to the supersonic nozzle. In this case, the pulsed flow modulation operation frequency is increased from about 0.25 Hz to typically 3-4 Hz, so that each portion of a GC peak that is transferred to the storage capillary column is transferred to the detector (MS) as a sharp sample flux pulse, with ~10-50 times reduced duration and as a result ~10-50 times higher peak signal. In this way the GC-MS with SMB sensitivity can be increased by the square root of the peak height increase up to 7 times. For this application, the volume of the storage column 4 should be correspondingly reduced by about an order of magnitude, and any dead volume in the system must be eliminated. This faster cycle time pulsed flow modulation sample introduction can be used with the MS when it is used in the single ion monitoring or MS-MS modes for improved sensitivity. We used this method with octafluoronaphthalene (OFN) and obtain 0.3 femtogram limit of detection with 25 times flow rate time compression Another appealing application is the combination of pulsed flow modulation GC-MS with SMB with the use of an ion trap as the mass analyzer (standard 3D or linear ion traps). In this case, the sample injection into a short deactivated transfer line that leads the sample to the supersonic nozzle can be synchronized in time with the electron ionization time (which is pulsed with ion traps GC-MS), and as a result the signal can be increased by the gas flow rate compression ratio factor of ~10-100. The SMB interface can accept flow rates up to 100 ml/min thereby enabling up to 100 times sample pulse compression with standard GC-MS column flow rate of 1 ml/min and up to 300 times with micro bore columns with 0.3 ml/min flow rates. Since GC-MS with SMB has ultra fast ion source response time and no ion source peak tailing, in view of the use of fly-through ion source, unlike with standard GC-MS, the pulsed flow modulation can proportionally increase the signal by the time compression factor. With ion trap mass analyzers, unlike with a standard quadruple mass analyzer, the signal increase does not affect the noise, and thus, the pulsed flow modulation could increase the sensitivity by a factor of up to 300, even in full scan mode. This way ion traps MS can achieve its long felt "dream" of achieving close to 100% duty cycle in both ion analysis and electron emission current utilization. Similarly, the pulsed flow modulation can be effectively used with time of flight mass analyzer, if it will be synchronized with pulsed electron emission or pulsed laser ionization.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A pulsed flow modulation gas chromatography mass spectrometry with supersonic molecular beams method for improved sample analysis, comprising the steps of:
   injecting a sample into a gas chromatograph;
   separating said sample compounds in the gas chromatograph by a first analytical column;
   eluting the sample from said first analytical column into a storage transfer column;
   passing a first gas pulse, of a relatively high flow rate carrier gas, through a gas line into a gas line connector also connecting the first analytical column and said storage transfer column;
   forming an increased pressure at the gas line connector by said high flow rate carrier gas pulse, to temporarily stop sample elution from said first analytical column;
   transferring the sample compounds in the storage transfer column with said high flow rate carrier gas pulse, into a second analytical column of a different polarity than the polarity of said first analytical column;
   providing a second gas pulse of intermediate carrier gas flow rate, of a duration longer than the duration of said first gas pulse for the separation in time of the sample compounds in said second analytical column;
   adjusting the time of said first gas pulse, second gas pulse and the ratio of second analytical column flow rate to first analytical column flow rate, to provide second analytical column chromatographic peak widths that are sufficiently broad to enable compatibility with a scanning speed of a mass spectrometer;
   adding makeup gas to the output gas flow of the second analytical column;
   reducing the flow rate of said added makeup gas to compensate for the increased second column flow rate;
   transferring said sample compounds via a heated transfer line into a supersonic nozzle;
   expanding said sample and combined second column and added make up gases from said supersonic nozzle for the formation of vibrationally cold sample compounds in a supersonic molecular beam;
   ionizing said sample compounds by electrons in a fly through ion source while they are contained in said supersonic molecular beam;
   analyzing the ions formed from said sample compounds in said supersonic molecular beam in a mass analyzer of a mass spectrometer;
   detecting said ions of said sample compounds after their mass analysis with an ion detector;
   processing the data obtained from the mass spectrometer after ion detection for identifying and/or quantifying the chemical content of said sample, and
   repeating the cycle of said first pulse of relatively high flow rate followed by said longer, second pulse of intermediate flow rate, in a repetitive fashion.

2. The method according to claim 1, wherein said mass analyzer of said mass spectrometer is a quadruple mass analyzer.

3. The method according to claim 1, wherein said mass analyzer of said mass spectrometer is an ion trap.

4. The method according to claim 1, wherein said second analytical column is replaced by a gas transfer line which is connected to said supersonic nozzle.

5. The method according to claim 3, wherein said first gas pulse is synchronized in time with the electron ionization time period of said ion trap mass spectrometer.

6. The method according to claim 1, wherein said first and second gas pulses are provided by a single gas source but with different flow rates obtained through the use of gas transfer lines with different flow impedances.

7. The method according to claim 1, wherein the flow rate of said first and second gas pulses are controlled by two separate flow controllers.

8. The method according to claim 1, wherein said longer, second gas pulse is provided through a second gas transfer line into a second gas connector connecting the output of the storage transfer column and the second analytical column to the second gas transfer line.

9. The method according to claim 1, wherein said gas pulses are of different pressures, wherein the first, shorter pulse provides a higher gas pressure than the second, longer pulse.

10. A pulsed flow modulation gas chromatograph mass spectrometer with supersonic molecular beams apparatus for improved sample analysis, comprising:
- a gas chromatograph with gas chromatograph injector for the analysis of sample compounds;
- a first analytical column in said gas chromatograph for the separation in-time of said sample compounds;
- sample storage means for temporarily storing said sample compounds after their elution from said first analytical column;
- a gas pulse generator for the generation of a high flow rate carrier gas pulse to be transferred through a gas line into a gas line connector also connecting the first analytical column and said sample storage means;
- pressure forming means for creating an increased pressure at said gas line connector by said high flow rate carrier gas pulse, to temporarily stop sample elution from said first analytical column;
- a conduit for transferring the sample compounds in said sample storage means with said pulsed high flow rate carrier gas, into a second analytical column, said second analytical column having a different polarity than the polarity of said first analytical column;
- a second gas pulse generator for generating a second gas pulse of a longer duration, for the separation of the sample compounds in said second analytical column;
- a transfer line for transferring the sample compounds eluting from the second analytical column into a supersonic nozzle;
- means for adding a makeup gas to the output gas flow of the second analytical column before said supersonic nozzle,
- means for reducing the flow rate of said added makeup gas to compensate for the increased second column flow rate;
- a supersonic nozzle for the expansion of said sample with the combined second analytical column and added makeup gas, for the formation of vibrationally cold sample compounds in a supersonic molecular beam;
- fly through electron ionization ion source for the ionization of said sample compounds while they are contained in said supersonic molecular beam;
- mass analyzer for analyzing the ions formed from said sample compounds in said supersonic molecular beam in a mass spectrometer;
- ion detector for the detection of said ions of said sample compounds after their mass analysis;
- means for data processing and presentation of the mass spectral data for identifying and/or quantifying the chemical content of said sample, and
- means for repeating the cycle of said first gas pulse of relatively high flow rate followed by said longer, second gas pulse of intermediate flow rate, in a repetitive fashion.

11. The apparatus according to claim 10, wherein said mass analyzer of said mass spectrometer is a quadruple mass analyzer.

12. The apparatus according to claim 10, wherein said mass analyzer of said mass spectrometer is an ion trap.

13. The apparatus according to claim 10, wherein said second analytical column is constituted by a gas transfer line connected to said supersonic nozzle.

14. The apparatus according to claim 12, further including means for synchronization in time of said first short time high flow rate carrier gas pulse with the electron ionization time periods of said ion trap mass spectrometer.

15. The apparatus according to claim 10, wherein shorter and longer gas pulses are fed from a single gas source having different flow rates.

16. The apparatus according to claim 10, wherein shorter and longer gas pulses are controlled by two separate flow controllers.

17. The apparatus according to claim 10, wherein said two gas pulses are different, the shorter pulse providing higher carrier gas pressure than the longer pulse.

* * * * *